United States Patent [19]
Radmand

[11] Patent Number: 5,791,471
[45] Date of Patent: Aug. 11, 1998

[54] DENTAL SHARPS CONTAINMENT DEVICE AND METHOD OF USING THE SAME "NEEDLE PROTECTION DEVICE" (NPD)

[76] Inventor: Reza Radmand, 1174 Amherst St. #207, Los Angeles, Calif. 90049

[21] Appl. No.: 904,730

[22] Filed: Aug. 1, 1997

[51] Int. Cl.⁶ .................................................. B65D 83/10
[52] U.S. Cl. .................................... 206/366; 220/908
[58] Field of Search ................................ 604/110, 192, 604/263; 206/364, 365, 366; 220/908, 910

[56] References Cited

U.S. PATENT DOCUMENTS 5,322,164  6/1994  Richardson et al. ............... 206/366
5,356,385  10/1994  Latini ................................. 206/366

*Primary Examiner*—Jacob K. Ackun
*Attorney, Agent, or Firm*—Graham & James LLP

[57] ABSTRACT

A dental sharps containment device comprises a housing unit having an insertion panel with an insertion hole therein, a removable protective sleeve, a gripping means for gripping a needle cap, and a disposable sharps container. The removable, protective sleeve is inserted into the insertion hole. When the needle apparatus is inserted into the protective sleeve, the protective sleeve guides the needle cap to a predetermined location inside the housing unit above the gripping means. The gripping means is operated to engage and firmly grip the needle cap so that when the syringe is pulled from the device, the needle pulls out of the needle cap. After use, the syringe is again inserted into the protective sleeve, which guides the needle back into the needle cap. When the needle has been used multiple times and is ready to be removed from the syringe for safe disposal, the syringe is twisted to unscrew it from the needle. The needle hub, which is frictionally attached or rotationally locked to the needle cap, is held by the gripped needle cap, and therefore does not rotate when the syringe is twisted. After the syringe detaches from the needle, the gripping means releases the needle cap containing the used needle allowing it to drop into a removable, disposable sharps container. Following use, the protective sleeve may be removed for disinfection.

22 Claims, 6 Drawing Sheets

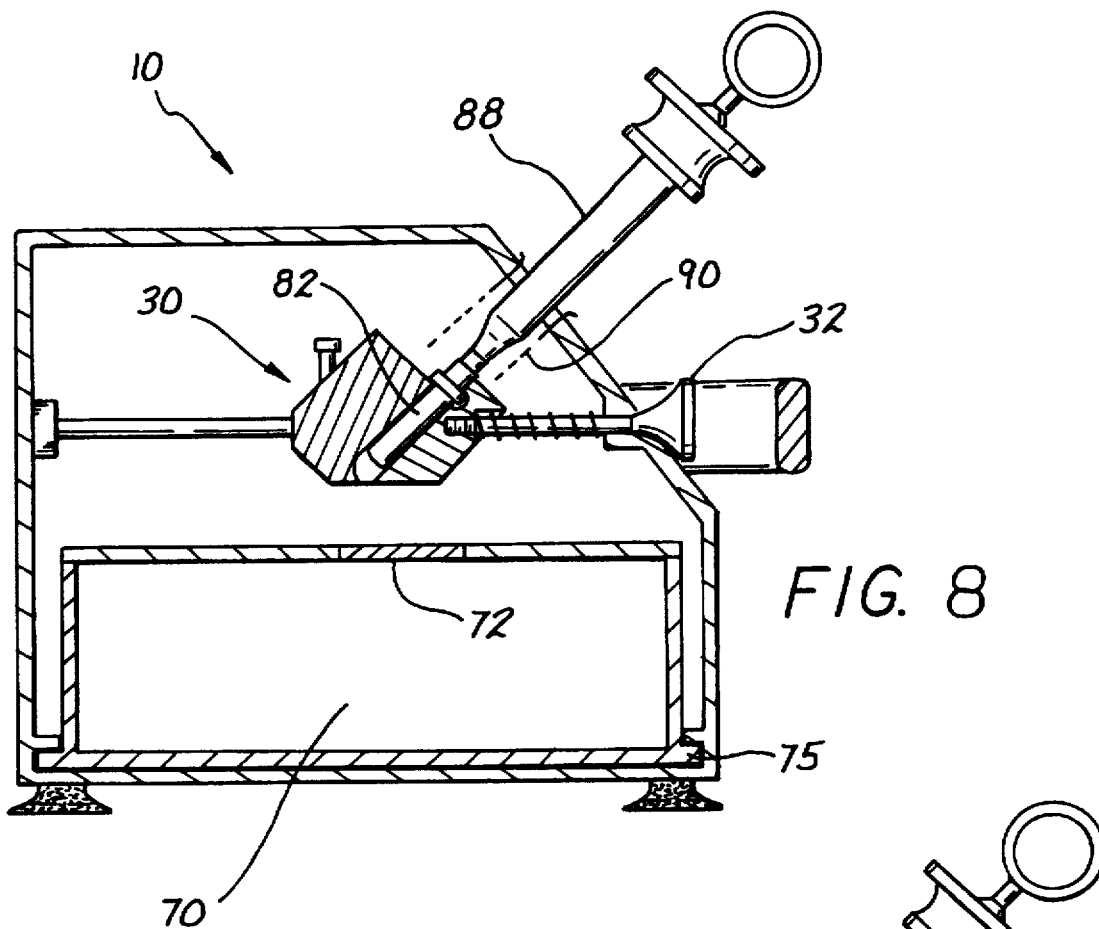
FIG. 8
FIG. 9
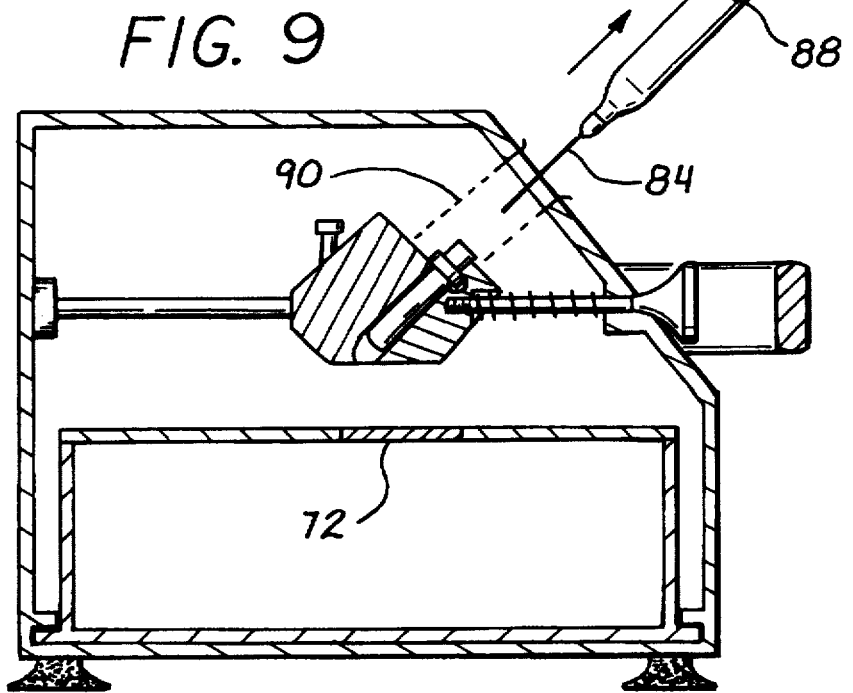

DENTAL SHARPS CONTAINMENT DEVICE AND METHOD OF USING THE SAME "NEEDLE PROTECTION DEVICE" (NPD)

BACKGROUND OF THE INVENTION

1. Field of the Invention

The present invention relates to a dental sharps containment device that allows dental professionals to safely recap, remove, discard, and dispose of hypodermic needles during and after a dental treatment.

2. Description of the Prior Art

With the widespread use of disposable medical implements, especially hypodermic needles, many devices have been developed to safely handle and dispose of such implements after use without risk of exposing any person handling the devices to injury, infection, or disease by puncture or contact with the used needles. It is normal practice in a hospital, for example, to provide disposal boxes to receive different types of medical refuse for disposal. One special class of items for disposal is commonly referred to as "sharps" and includes used hypodermic needles. Many different kinds of sharps containers have been devised. Currently available sharps containers are gravity dependent in that the item for disposal is dropped or inserted into the container and falls to the bottom of the container. As will be discussed in the next section, many devices have been invented to safely remove used hypodermic needles from the syringes. However, currently available sharps/needle containment devices do not allow the recapping of the needle during a dental treatment that requires multiple uses of a given needle-syringe on the one patient, such as providing multiple injections of Novocain.

Everhart, "Device and Method of Removal and Storage of Syringe Needle," U.S. Pat. No. 5,275,280 (1994) discloses a device and method for removal and storage of syringe needles. The device comprises a housing containing a pair of resiliently hinged jaws which are operated by a lever. The jaws hold the hub of a needle with sufficient force to permit the user to rotate the barrel of a syringe for needle removal, after which the lever is used to open the jaws and allow the used needle to fall into the housing for safe disposal.

Lee, "Sharps Container," U.S. Pat. No. 5,145,063 (1992) discloses a sharps container having an opening through which needles, syringes and the like are inserted. The opening includes a spring-biased door which maintains the container in a closed condition except when an article is actually being inserted.

Heimreid, "Arrangement in Connection with a Rack for Orderly Storage and/or for Keeping Syringes with a Luer Tip Ready for Use," U.S. Pat. No. 5,099,992 (1992) discloses an arrangement, which comprises a plurality of supports and receptacles for holding syringes and needles in an upright manner ready for use.

Baudry, et al., "Box for Gathering Dangerous Refuse," U.S. Pat. No. 5,046,613 (1991) discloses a box for gathering dangerous refuse which includes a slide closure having means for gripping needles and holding them for removal from a syringe for subsequent disposal in the box.

Mostarda, et al., "Safety Apparatus for Extracting Hypodermic Needles from the Respective Syringe," U.S. Pat. No. 5,046,612 (1991) discloses a receptacle having a slot for accepting a needle which is mounted on a syringe. Retention means at the end of the slot engages the needle to hold it in position while it is removed from the syringe whereupon the needle falls into a container.

Hernandez, "Device for Holding a Medical Syringe," U.S. Pat. No. 4,938,354 (1990) discloses a device for holding a medical syringe which comprises a base unit capable of holding a needle cover in an inclined position while the syringe and needle combination are withdrawn therefrom. An annular elastic collar assists in holding the needle cover in place during this operation.

Nosanchuk, "Needle Cap Replacement Device," U.S. Pat. No. 4,875,583 (1989) discloses a block or stand of weighted plastic having one or more recesses for the receipt and retention of needle caps. The recesses may be different sizes and shapes to accommodate caps of varying sizes. The block may also be provided with an opening therethrough having a bore sufficient to permit passage of the used syringe for disposal into a receptacle.

Coulombe, "Medical Supplies Container," U.S. Pat. No. 4,844,249 (1989) discloses a medical supplies container which includes apertures designed to hold needle covers while a syringe is removed and replaced.

Hall, et al., "Medical Container," U.S. Pat. No. 4,802,579 (1989) discloses a medical container for disposal of used needles and includes a disposable housing for receiving used needles following their removal from syringes. The container includes a needle release area having a port with a restricted area for gripping the needle collar thereby providing a mechanical advantage for easy needle removal.

Bruno, "Containment Device for Safely Removing, Storing and Ultimately Disposing of Needles from Hypodermic Needle/Syringe Assemblies," U.S. Pat. No. 4,801,013 (1989) discloses a needle removal and storage device for removing needles from hypodermic needle/syringe assemblies and automatically receiving and safely storing removed needles within the device.

However, none of the prior art patents discloses a device that safely allows a dental professional to use the same needle on the same patient multiple times without changing the needle or manually recapping it after each use, and also allows the dental professional to remove and dispose the used needle safely and conveniently after the final use.

Therefore, there exists a need for a device that recaps the needle safely and conveniently during the dental treatment that requires multiple uses of the same needle on the same patient.

There also exists a need that such device should also be able to safely remove and store the used needles for disposal.

BRIEF SUMMARY OF THE INVENTION

The present invention, a dental needle containment device, comprises a housing unit having an insertion panel with insertion holes therein; a removable, protective sleeve; a gripping mechanism for gripping a needle cap; a secondary opening for the disposal of sutures and blades, and an integral disposable sharps container. The removable, protective sleeve is first inserted into the insertion hole before a needle apparatus is inserted into the protective sleeve. The needle apparatus typically has a syringe, a needle hub, a needle, and a needle cap covering the needle and attached by frictional engagement with the needle hub portion of the needle. The gripping mechanism is mounted inside the housing unit, and has two platforms for engaging the needle cap. When the needle apparatus is inserted into the protective sleeve, the protective sleeve guides the needle cap to a predetermined location inside the housing unit. The tip of the needle cap contacts the gripping mechanism. The top platform of the gripping mechanism has a moveable spring loaded part, which can be operated to move vertically. The gripping mechanism then engages and firmly grips the needle cap so that when the syringe is pulled out of the protective sleeve, the needle pulls out of the needle cap which remains within the grasp of the gripping device.

After use, the syringe is inserted back into the protective sleeve, which guides the needle back into the needle cap. When the needle-syringe has been used multiple times and is ready to be removed from the syringe for safe disposal, the syringe can be twisted to unscrew it from the needle. The needle cap, which is frictionally attached to the needle hub of the needle, is held by the gripping mechanism, and therefore does not rotate when the syringe is twisted. As the syringe is twisted, the needle detaches from the syringe. At that time, the gripping mechanism releases the needle cap containing the used needle allowing it to drop it into a removable, disposable sharps container.

This system which keeps the needle cap in an enclosed unit during the dental treatment requiring multiple administrations of the needle apparatus promotes safety, economy and convenience for both the dentist and the patient. After each patient, the protective sleeve can be removed for autoclaving, thereby removing any chance of cross-contamination. After the disposable sharps container fills to a predetermined capacity, a cover is irreversibly placed thereon for safety. The sharps container can then be disposed of by incineration or other customary means.

The invention may be better visualized by now turning the following drawings wherein like elements are referenced by like numerals.

BRIEF DESCRIPTION OF THE DRAWINGS

FIG. 8 is a diagrammatic cross-section of the containment device with a syringe bearing a capped needle inserted into the gripping mechanism;

FIG. 9 is a cross-section similar to FIG. 8 with the syringe withdrawn from the device to expose the needle;

The invention and its various embodiments may now be understood in the following detailed description of the illustrated embodiment.

DETAILED DESCRIPTION OF THE PREFERRED EMBODIMENTS

Figure 1:
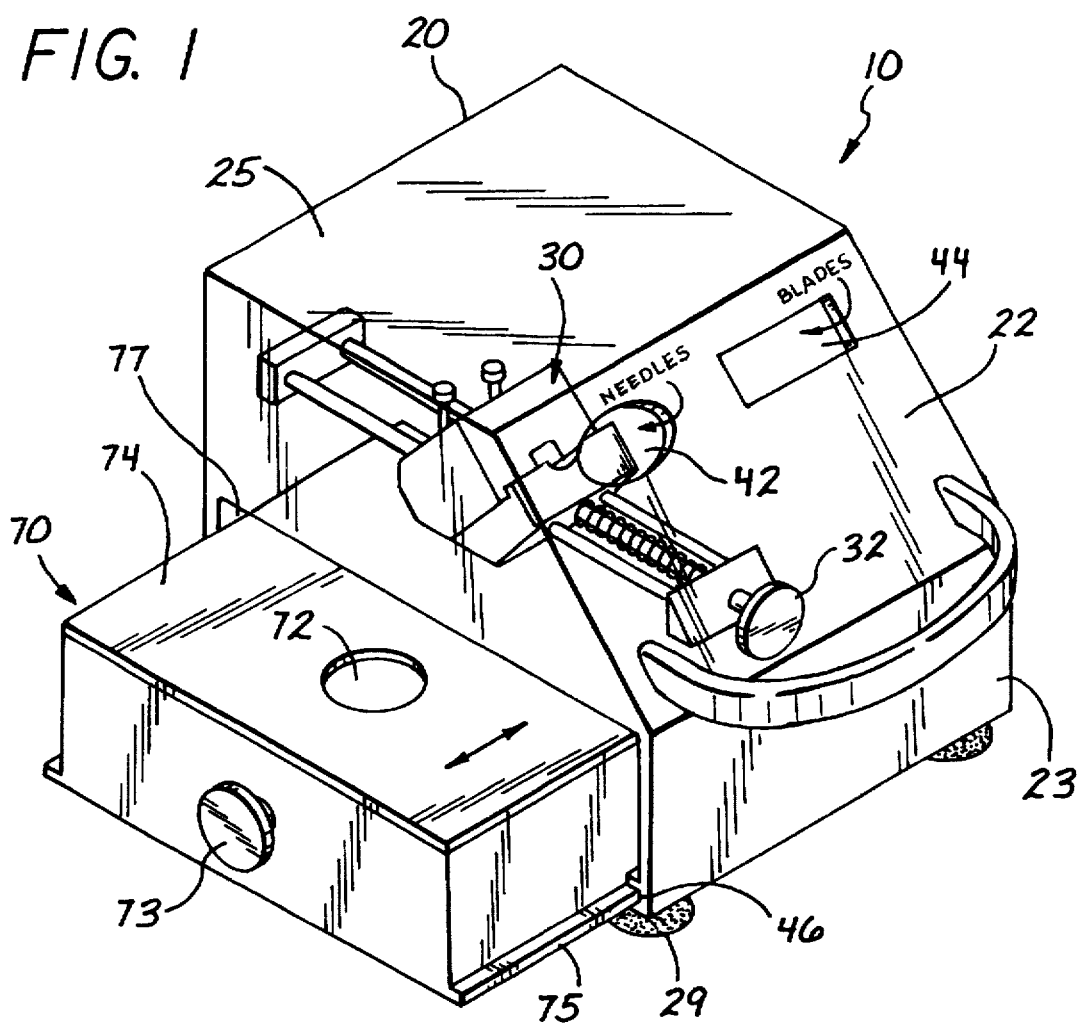
FIG. 1 is a perspective view of a dental sharps containment device.

As shown in FIG. 1, a dental sharps containment device 10 comprises a housing unit 20 having an insertion panel 22 with an insertion hole 42 therein, a removable and protective sleeve 90, a gripping mechanism 30 for gripping a needle cap 82, a removable disposable sharps container 70, a second disposal hole 44 for other sharps, i.e. used blades and sutures, and four suction cup-like structures 29 for securing the unit to the working table. The unit 20 can also be mounted onto the wall, if so desired.

Figure 10:
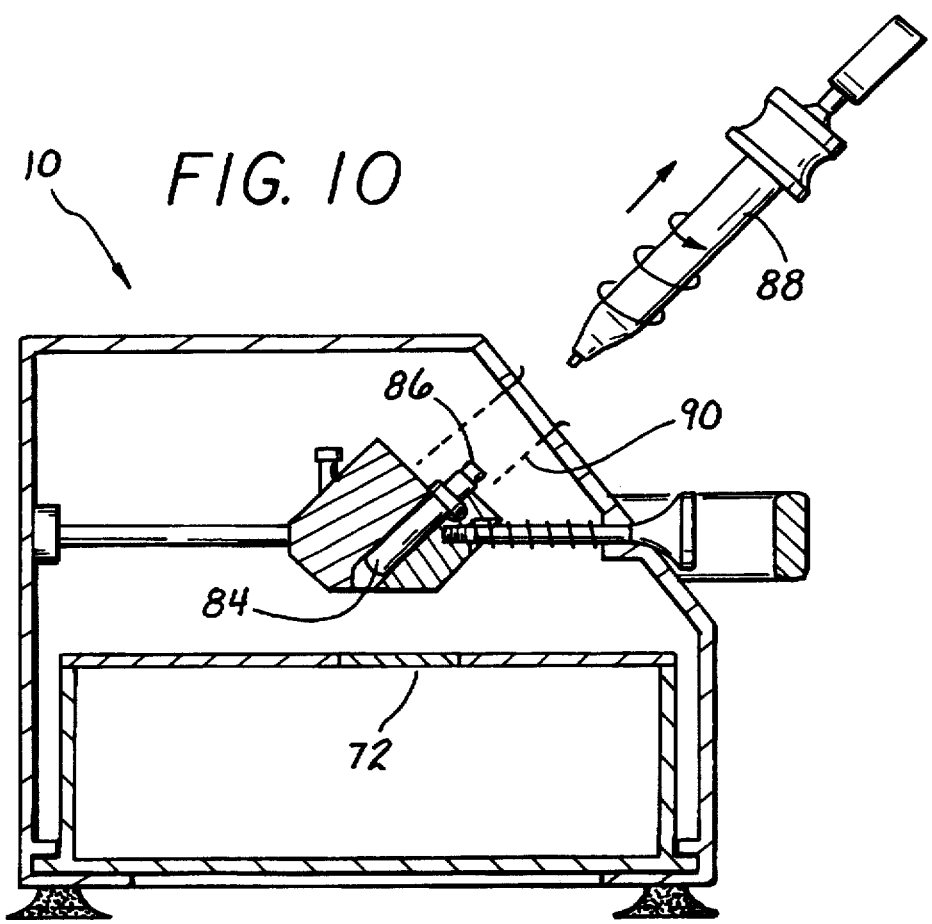
FIG. 10 shows the syringe being removed from the capped needle following reinsertion of the syringe and needle into the containment device it has been reinserted into the containment device.
Figure 11:
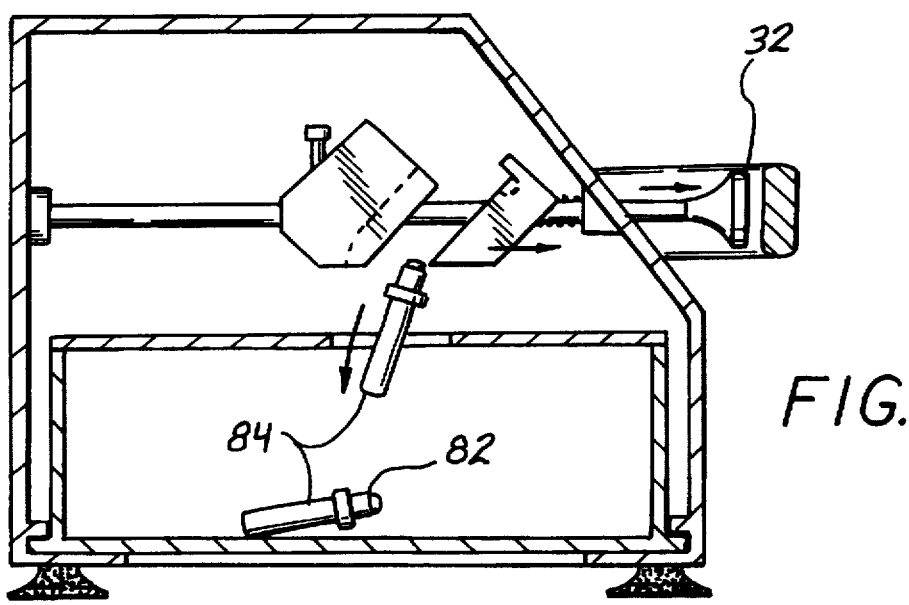
FIG. 11 shows the containment device being operated to deposit the used needle and cap into the disposable container.

In use, the removable, protective sleeve 90 is first inserted into the insertion hole 42. A needle apparatus 80 is then inserted into the protective sleeve 90, and the protective sleeve guides 90 the needle cap 82 through the gripping mechanism 30 to a predetermined location inside the housing unit 20. The needle cap 82 is located just above or even just passes through an opening 72 into the removable sharps container 70 (see FIG. 8). The gripping mechanism 30 operates to engage and firmly grip the needle cap 82 so that when the syringe 88 is pulled out (FIG. 9), the needle 84 can be pulled out of the needle cap 82. After use, the syringe 88 can be inserted back into the protective sleeve 90, which guides the needle 84 back into the needle cap 82. When the needle 84 has been used multiple times and is ready to be removed from the syringe 88 for safe disposal, the syringe 88 is twisted to unscrew it from the needle 84 (FIG. 10). The needle hub 86, which is frictionally attached or rotationally locked to the needle cap 82, is held by the gripped needle cap 82, and, therefore, does not rotate when the syringe 88 is twisted. As the syringe 88 is twisted, the needle 84 detaches from the syringe 88 and the gripping mechanism 30 is operated to release the needle cap 82 and the contained the used needle 84 allowing them drop it into a removable, disposable sharps container 70 (FIG. 11).

The protective sleeve 90 performs a dual function. It guides the needle cap 82 into the gripping mechanism 30 and it protects the interior of the device 10 from becoming contaminated and passing contamination onto subsequent syringes 88. On initial insertion into the device 10 the syringe 88 will be clean. Therefore, the needle cap 82 will be uncontaminated and will not be capable of contaminating the griping mechanism 30. However, after use, the needle 84 and even the syringe body 88 may be contaminated. Conceivably this contamination could be deposited within the unit 10 and contaminate subsequent syringes 88. However, if after each patient the protective sleeve 90 is removed for autoclaving or other similar sterilization contamination problems will be avoided. It will be appreciated that by constraining the insertion hole 42 and/or adding a permanent guide, the needle cap 82 could be successfully guided into the gripping mechanism 30 without use of the protective sleeve 90. Thus, the device 10 could be made without the protective sleeve 90. For this reason the sleeve 90 is shown as dotted in FIG. 8–FIG. 11. However, it remains that the preferred design employs the removable protective sleeve 90.

Additional details will help the reader understand the present invention. A preferred embodiment contains a second insertion hole 44, for other sharps, i.e. blades and sutures on the insertion panel 22. The housing unit 20 is a substantially hollow container defined by insertion panels 22, a top surface 25, an upper side wall 26, an opposing closed side wall 27, a front wall 23, a back wall 24, and a bottom surface 28. A disposable container entry 77 is defined on one side of housing unit 20, defined by the peripheries of back wall 24, front wall 23, bottom surface 28, and the lower edge of upper side wall 26. Housing unit 20 is preferably made from a standard puncture-resistant, incineratable material that is widely used in making currently available sharps containers and devices such as high density polyethylene, polypropylene or some similar moldable plastic material. Of course, sheet metal or other like materials would also be suitable.

Figure 2:
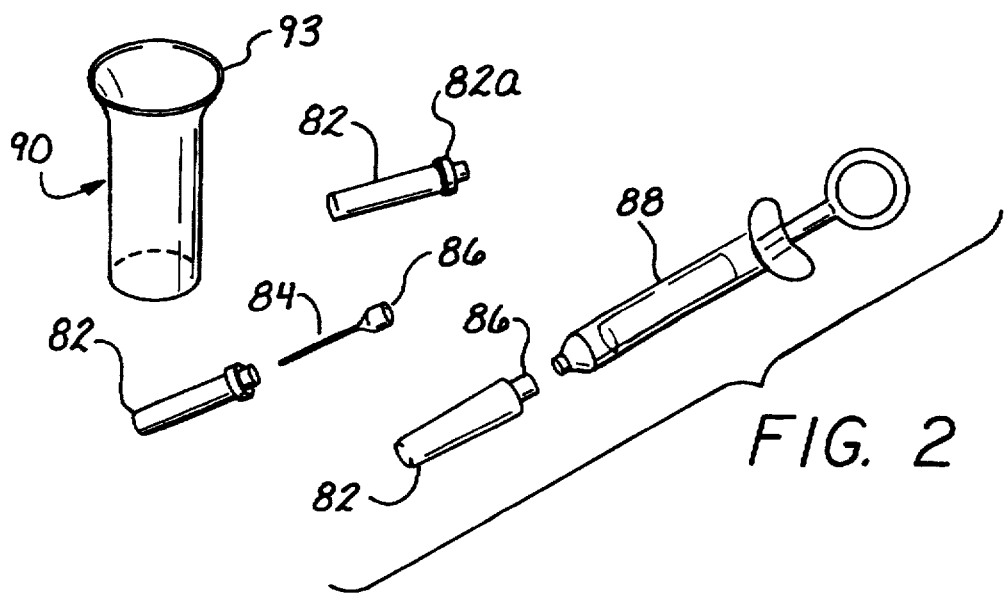
FIG. 2 is a perspective view of a removable, protective sleeve and the needle-syringe apparatus shown in isolation from the containment device.

The insertion panel 22 has the first insertion hole 42 defined therein. The insertion panel 22 bears the second insertion hole 44. The removable protective sleeve 90 is sized for insertion into the first insertion hole 42. FIG. 2 shows the removable protective sleeve 90 in perspective view with a needle 84 inside of a needle cap 82 and connected by a needle hub 86 to the syringe 88 of a needle apparatus generally denoted by reference numeral 80. The needle apparatus 80 is inserted into the sleeve 90 as shown in exploded perspective view of FIG. 8. In the preferred embodiment, the protective sleeve 90 is an elongated and tapered cylinder made from autoclavable material. The removable protective sleeve 90 may have a radially projecting flange to mate with the insertion panel 22. Other configurations of the sleeve 90 will be apparent to one of skill in the art and are equally contemplated by the present invention so long as they serve to guide the needle cap into the gripping mechanism 10 and provide a removable structure to prevent contamination of the interior of the device 10.

Figure 3:
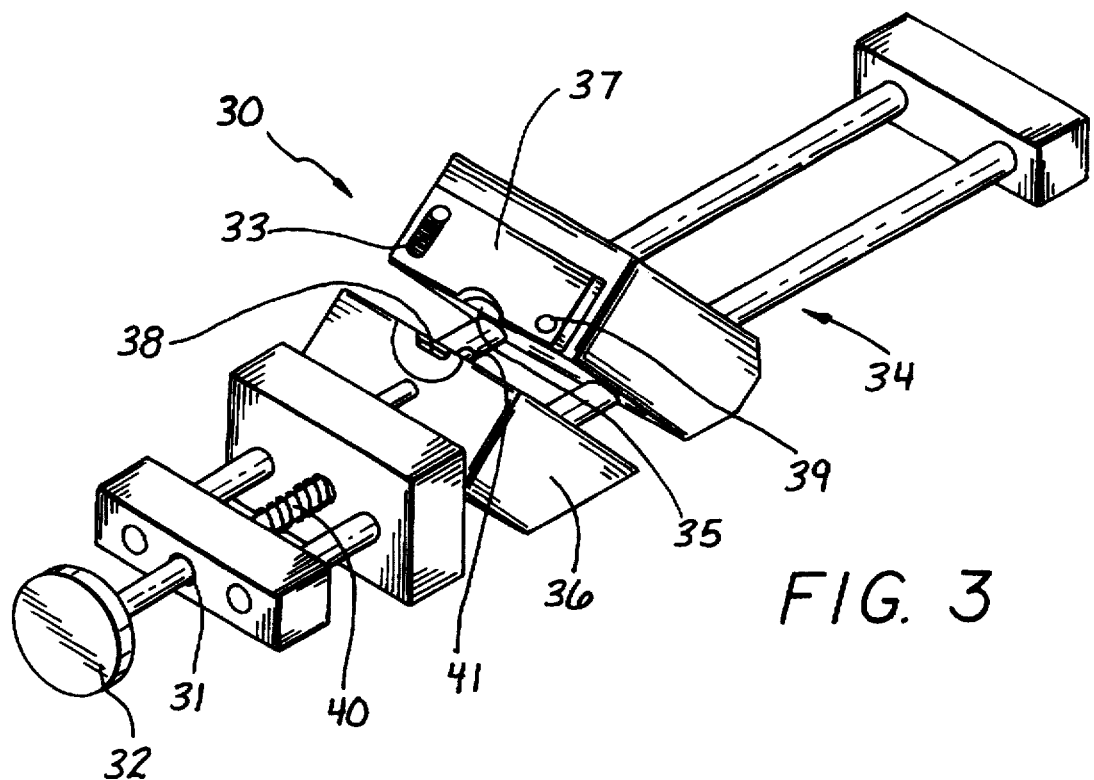
FIG. 3 is a top sectional view of the gripping mechanism in an open position.
Figure 4:
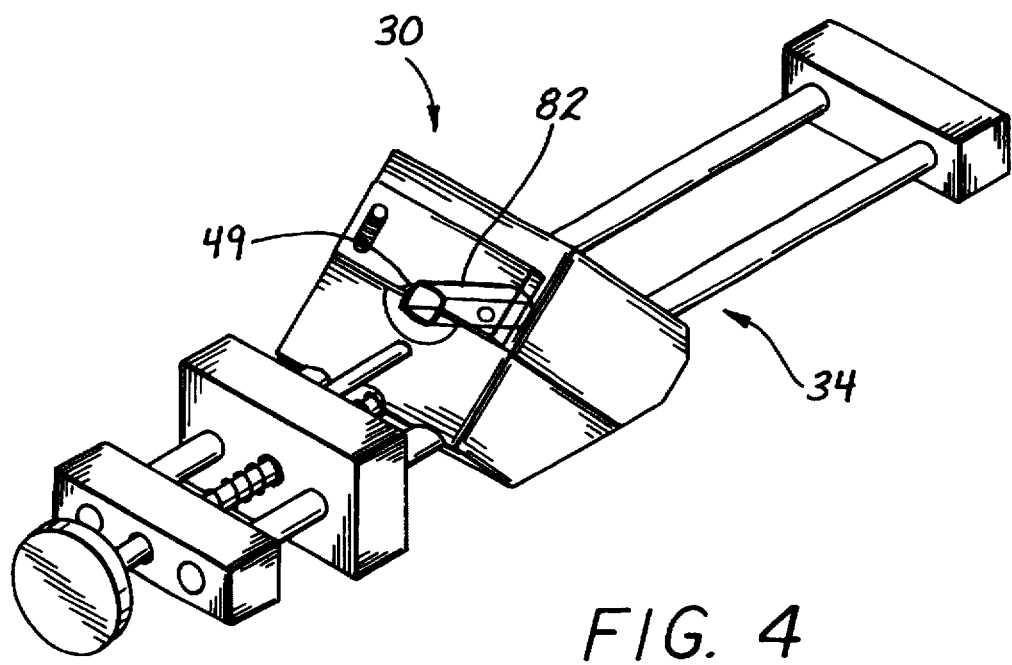
FIG. 4 is a top sectional view of the gripping mechanism of FIG. 3 with a needle cap gripped between two plates.

FIGS. 3 and 4 show stages of operation of the gripping mechanism 30. The gripping mechanism 30 comprises a stationary part 34 and a movable arm 36. One end of the stationary part 34 is fixedly attached to inside of the back wall 24, and the other end of stationary part 34 defines a stationary edge 35, which has a spring loaded plate 37 attached on one side. During function, the plate 37 rotates ever so slightly in an upward and downward direction on an axis 39. The exterior end of the movable arm 36 forms a grip handle 32, which extends out of housing unit 20 through an opening 31 defined through the front wall 23. The opposing interior end of the movable arm 36 has a movable arm gripping edge 38. The stationary part 34 and the moveable arm 36 can be supported by structural supports (e.g. rails) or an interior wall (not shown) within the housing unit 20. The stationary part 34 and the movable arm 36 are, in any case, supported or aligned horizontally with each other inside the housing unit 20. The movable arm edge 38 and stationary part edge 35 face each other, cooperate to form a tight grip on the center of edge 35, plate 37 and on the center of edge 38. This forms an opening that is slightly smaller than the maximum diameter of the smallest needle cap 82 expected to be placed between them. The separation between the edges 35 and 38 therefore defines a pilot hole 49 into which the tip of needle cap 82 is centered or disposed.

The basic structure of the containment device 10 now having been described, consider the mode of its intended use. The needle apparatus 80 includes a syringe 88, a needle hub 86, a needle 84 and a needle cap 82 as shown in FIG. 3. When a dental professional is ready to use the needle apparatus 80, for instance, for injecting a local anesthetic into a patient, he or she will first put the anesthetic capsule inside the syringe 88 and subsequently place the sealed needle 82 and cap 84 assembly on the syringe 88. The protective sleeve 90 is placed in the insertion hole 42. Thereafter, the needle apparatus 80 is inserted into the protective sleeve 90, which guides the needle cap 82 downward into the pilot hole 49. Since the exterior diameter of the needle cap 82 is smaller than the diameter of the sleeve 90, the needle cap 82 passes through the sleeve 90 and protrudes from the internal end of the sleeve 90. The protruding needle cap 82 is position near or in the pilot hole 49 which is formed between the two edges 35, 38 of the gripping mechanism 30. As the needle cap 82 is forced into the pilot hole 49, the edges 35 and 38 are forced apart until the needle cap 82 is engaged by a quadrangular recessed portion of at the center of the superior edge 38 of the arm 36 formed when a bevel initially allows the plates 35 and 37 to separate slightly as the plate 37 pivots on the axis 39. An adjustable spring loaded mechanism 33 determines the tension necessary to allow the plate 37 to pivot relative to the stationary plate 35. This tension allows the gripping mechanism 30 to maintain its grip on the needle cap 82. It must be understood that while the plate 37 is shown on the stationary part 34, the invention also contemplates placement of the pivoting plate 37 on the movable arm 36.

To administer an anesthetic, the dental professional needs only to pull the needle apparatus 80 from the dental sharps containment device 10 (FIG. 9). The gripping mechanism 30 which grips the needle cap 82 will prevent the needle cap 82 from following the needle apparatus 80 when the needle 84, which, through its needle hub 86, is attached to syringe 88, is pulled from the needle cap 82.

After using the needle apparatus 80, the dental professional can reinsert the needle apparatus 80 back into the protective sleeve 90. Although the needle 84 is exposed at this point, the user does not have to touch anything to recap or reinsert the needle 84 into the stationary needle cap 82. Inserting the needle apparatus 80 into the protective sleeve 90, guides the needle apparatus 80 downward, and the needle 84 penetrates smoothly into the needle cap 82. The needle cap 82 frictionally engages the needle hub 86 and completely surrounds the needle 84, while being maintained in a gripped position. The needle apparatus 80 is once again positioned safely with its needle protected, ready for its next administration of anesthetic to the patient. The gripping of needle cap 82 in a secure position allows multiple uses of the same needle on the same patient.

When the needle 84 has been used multiple times and is ready to be removed from the syringe 88 for safe disposal, the syringe 88 can be twisted to unscrew the needle 84 (FIG. 10). The needle cap 82, which is attached to the needle 84 by frictional engagement with the needle hub 86, is firmly held by the gripping mechanism 30, and thus does not rotate when the syringe 88 is twisted. The needle hub 86 may be rotationally locked to the needle cap 82 either by means of a tight friction fit or by one or more flats or a hexagonal nut and socket engagement between the needle cap 82 and the hub 86. After the syringe 88 is twisted sufficiently, the needle hub 86 detaches from the syringe 88. At this point, needle 84 is still contained inside the needle cap 82, with only a portion of the needle hub 86 exposed.

When the user pulls the grip handle 32 away from the closed position as shown in FIG. 11, a spring member 40 is compressed, and the stationary plate edge 35 and the movable plate edge 36 pull apart, creating a widened gap therebetween. The needle cap 82 containing the used needle 84 is pushed by a special horizontal lever 41 which forces the needle cap 82 including the needle 84 assembly, out of its engagement with the gripping mechanism 30 allowing it to drop into the sharps disposable container 70 as shown in FIG. 11. After each patient, the protective sleeve 90 is removed for autoclaving or another sterilization procedure. Obviously, the protective sleeve 90 can itself be disposable and be replaced by a new sleeve for each patient.

Figure 5:
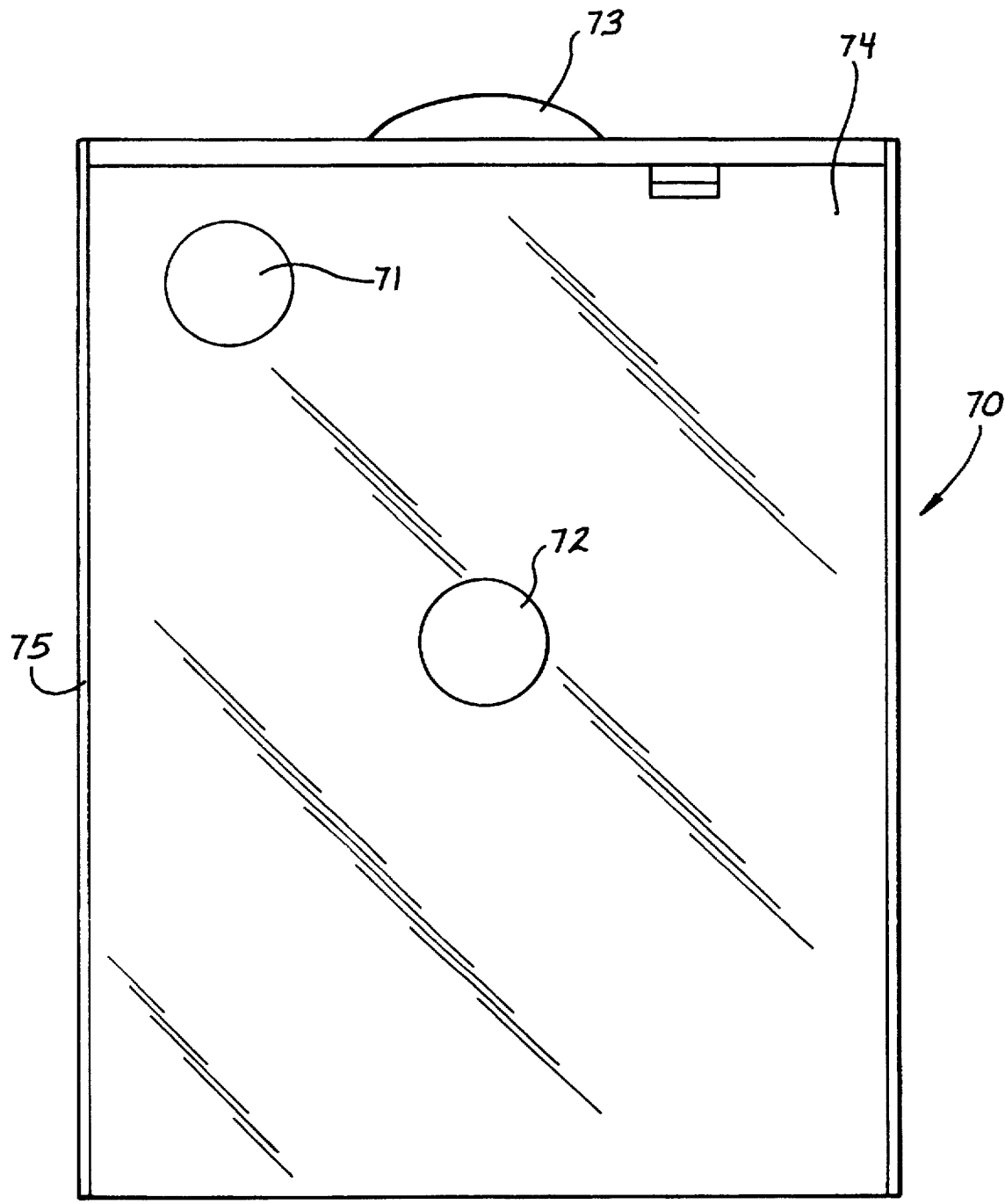
FIG. 5 is a top view of a sharps disposable container showing the openings for needles and other sharps (note this sharps container is the alternative front entry design shown in FIG. 7)
Figure 7:
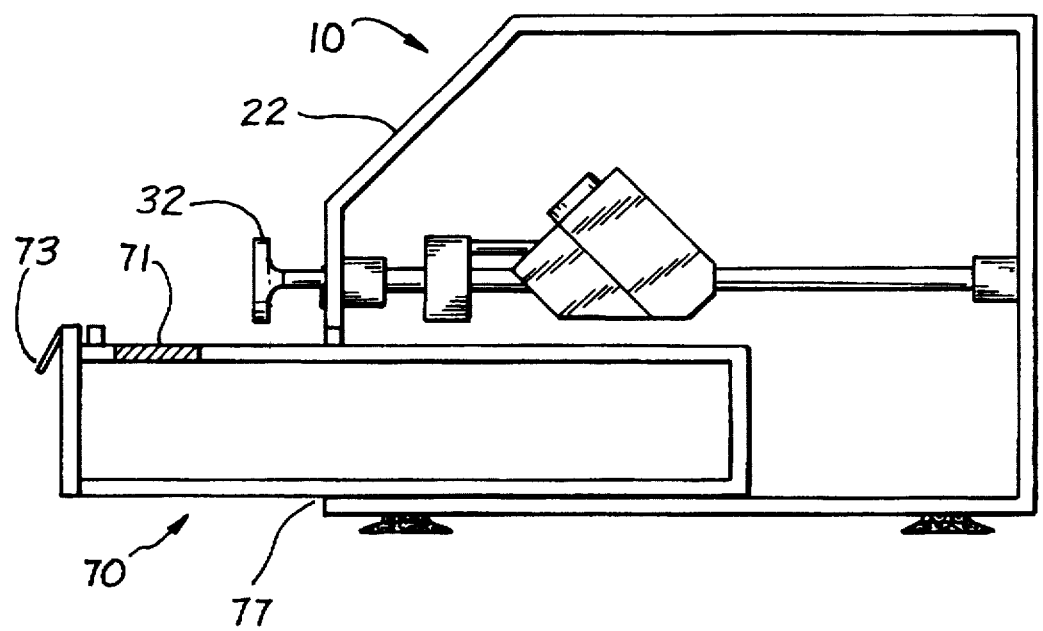
FIG. 7 is a sectional view of an alternative embodiment of the containment device wherein the disposable container is withdrawn from the front of the device.

FIG. 5 shows a top view of a sharps disposable container 70, which is a hollow container which is inserted into the housing unit 20 through a disposable container entry 77 which may be on a side wall (FIG. 1) or the front (FIG. 7) of the unit 10. In a preferred embodiment, a male rail member 75 is attached to each side of the disposable container 70 and slides into a pair of female rail receiving members 46 attached on inside of the front wall and the back wall, respectively as shown in FIG. 1. After the sharps disposable container 70 is filled to its capacity or to a predetermined limit such as 75% of total capacity, it is removed by pulling a container knob 73 attached on one side of the disposable container 70. To seal the disposable container 70, a container cover may be provided. Alternatively, caps to close openings in the container 70 may be used. Due to the danger posed by the content of the disposable container 70, a locking means that can irreversibly latch the container cover 74 to the sharps container 70 is necessary. The sharps disposable container 70 can then be safely removed to be incinerated.

Figure 6:
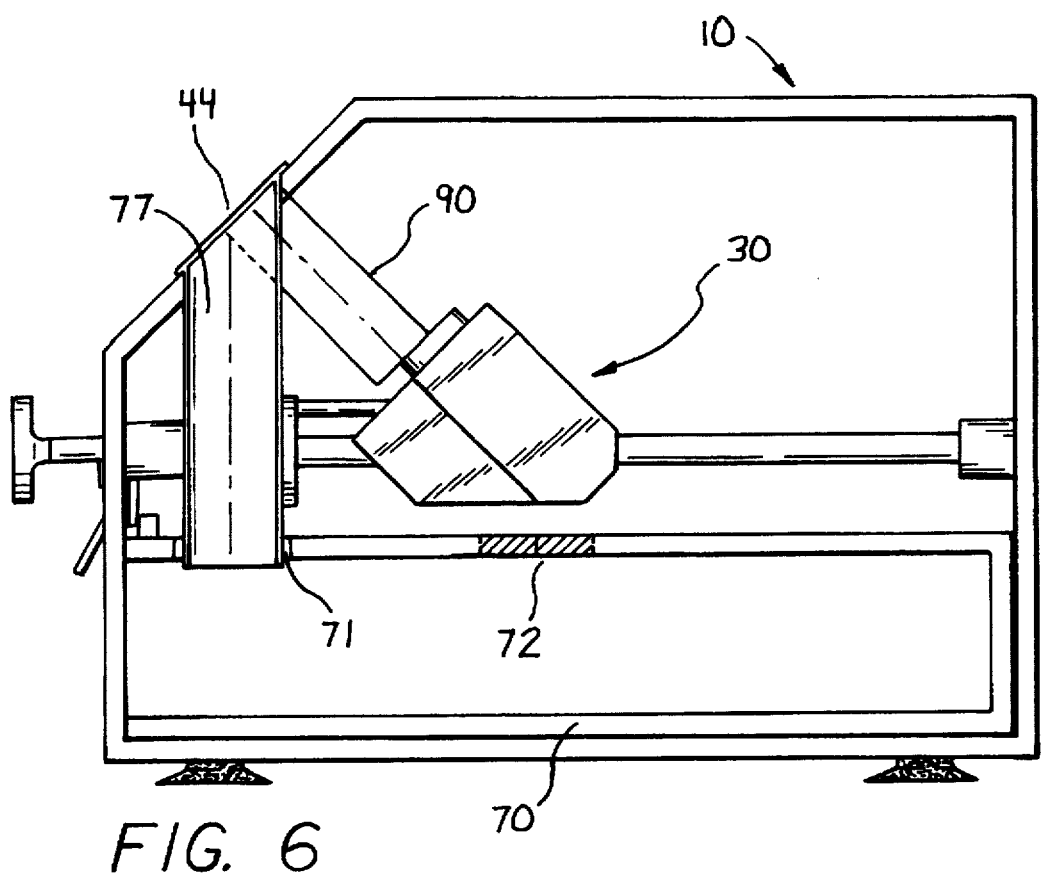
FIG. 6 is a sectional view of the containment device showing an insert that ensures that other sharps enter the disposable container.

In alternative preferred embodiment of the invention depicted in the perspective view of FIG. 1, the insertion panel 22 includes a second sharps disposal hole 44, for disposal of other dental sharps such as surgical blades and suture needles. These sharps are discarded into the second sharps disposal hole 44, through which they drop into the sharps disposable container 70 below through a second disposal hole 71. The disposal hole 44 has a disposable insert 78 made out of incineratable plastic which lines the canal of the insertion hole 44 and leads to the disposal hole 71 of the disposable sharps container 70 (see FIG. 6).

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A needle containment device for use with a needle apparatus provided with a needle and needle cap comprising:

a housing unit having a removable sharps container disposed within and an insertion panel, said insertion panel having an insertion hole defined therein;

a removable protective sleeve having a larger proximal opening and a smaller distal opening inserted through said insertion hole such that said removable protective sleeve is held in position by said insertion hole and extends downwardly into said housing unit for receiving and guiding a needle cap to a predetermined location inside said housing unit when a needle apparatus is inserted into said housing unit through said larger opening of said removable protective sleeve; and a gripping means for selectively gripping and releasing said needle cap disposed inside said housing unit, wherein said sharps disposable container is positioned below said gripping means to receive and contain said needle cap and needle after said needle cap and needle are detached from said needle apparatus and released by the gripping means.

2. The needle containment device of claim 1 wherein said removable protective sleeve is autoclavable.

3. The needle containment device of claim 2 wherein said removable protective sleeve is an elongated cylinder.

4. The needle containment device of claim 1 wherein said removable protective sleeve further comprises a flange around said proximal opening.

5. The needle containment device of claim 4 wherein said removable protective sleeve is autoclavable.

6. The needle containment device of claim 5 wherein said removable protective sleeve is a hollow cylinder.

7. The needle containment device of claim 1 wherein said insertion panel further includes a sharps disposal opening, whereby sharps may be discarded therethrough into said sharps container positioned below.

8. The needle containment device of claim 7 further comprising an insert to guide sharps from the sharps disposal opening into the sharps container.

9. The needle containment device of claim 1 wherein said gripping means comprises a stationary portion and a movable portion, said stationary portion and said movable portion each provided with a gripping edge, said gripping edges of said stationary and movable portions being urged toward each other so that said needle cap is gripped between said edges when said needle cap is inserted through said insertion hole.

10. The needle containment device of claim 9 wherein said gripping means further comprises a pivoting plate on one of said gripping edges, said pivoting plate forming a contact surface for interaction with said needle cap when said needle cap is inserted through said insertion hole.

11. The needle containment device of claim 10 wherein said pivoting plate pivots with respect to said edge on a single axis and the pivoting is regulated by an adjustable spring.

12. The needle containment device of claim 1 wherein said sharps container further comprises a container cover and a locking means to irreversibly attach said container cover to said sharps container.

13. The needle containment device of claim 12 wherein said locking means comprises a one way locking stopper which is inserted into the sharps container disposal holes to irreversibly lock into said sharps container holes.

14. The needle containment device of claim 1 further comprises an entry defined in said containment and wherein said sharps disposable container comprises a knob attached to said sharps disposable container for pulling and pushing said sharps disposable container through said disposable container entry.

15. A method of recapping and removing a needle during dental treatment by using a needle containment device having a housing unit with an insertion hole thereon; a gripping means with a handle for selectively gripping and releasing a needle cap; and a removable sharps disposable container positioned below said gripping means, said method comprising the steps of:

inserting an removable protective sleeve into said insertion hole, said removable protective sleeve allowing for inserting a needle apparatus with said needle cap attached to said needle apparatus into said removable protective sleeve until said needle cap contacts said gripping means;

engaging said needle cap by said gripping means;

pulling said needle apparatus upwardly to extract a needle from said needle cap;

inserting said needle apparatus back into said removable protective sleeve after use and guiding said needle into said needle cap held in position by said gripping means;

repeating said steps of pulling and inserting until said dental treatment is completed;

twisting said needle apparatus to detach said needle cap from said needle apparatus;

operating said gripping means to release said needle cap and said needle contained therein to allow their descent into said sharps disposable container below; and removing said removable protective sleeve for sterilization.

16. A needle containment device for use with a needle apparatus having a disposable portion comprising:

a housing unit;

an removable protective sleeve disposed in said housing unit for receiving and guiding a disposable portion of a needle apparatus to a predetermined location inside said housing unit; and a gripping means for selectively gripping and selectively releasing said disposable portion when disposed inside said housing unit.

17. The needle containment device of claim 16 wherein said protective sleeve is autoclavable.

18. The needle containment device of claim 16 wherein said housing unit further comprises a removable sharps container.

19. The needle containment device of claim 16 further comprising a cover for sealing said housing unit when said removable protective sleeve is not disposed therein.

20. The needle containment device of claim 16 wherein said gripping means comprises a stationary portion and a movable portion, each provided with a gripping edge, said edges being urged toward each other so that said disposable portion is gripped between said edges.

21. The needle containment device of claim 20 wherein said gripping edges are arcuate and define a pilot hole between them into which said protective sleeve guides said disposable portion of said needle apparatus.

22. A needle containment device for use with a needle apparatus having a disposable portion comprising:

a housing unit;

a removable sharps container disposed within said housing unit; and a gripping means for selectively gripping and selectively releasing a disposable portion of a needle apparatus when said disposable portion is disposed inside said housing unit, said gripping means comprising a stationary portion and a movable portion, said stationary portion and said movable portion each provided with a gripping edge, said gripping edges of said stationary and movable portions being urged toward each other so that said disposable portion is gripped between said edges.

* * * * *